United States Patent [19]

Sprague et al.

[11] 3,984,474
[45] Oct. 5, 1976

[54] 4,5-SECOANDROSTANES

[75] Inventors: Peter W. Sprague, Titusville; Christopher M. Cimarusti, Hamilton, both of N.J.

[73] Assignee: E. R. Squibb & Sons, Inc., Princeton, N.J.

[22] Filed: May 30, 1975

[21] Appl. No.: 582,014

[52] U.S. Cl. ............... 260/586 E; 260/617 F; 260/631 R; 260/648 R; 260/666 PY; 424/331; 424/343; 424/352; 424/356
[51] Int. Cl.² .......................................... C07C 49/27
[58] Field of Search ......... 260/586 E, 617 F, 631 R, 260/648 R, 666 PY

[56] References Cited
UNITED STATES PATENTS 3,793,374  2/1974  Micheli ........................ 260/586 E

*Primary Examiner*—Gerald A. Schwartz
*Attorney, Agent, or Firm*—Lawrence S. Levinson; Merle J. Smith; Donald J. Barrack

[57] ABSTRACT

4,5-Secoandrostanes having the formula

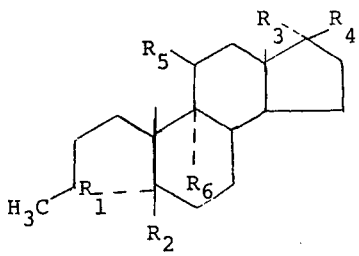

have useful anti-inflammatory activity wherein $R_1$ is hydrogen and $R_2$ is hydroxyl, $R_1$ is hydroxyl and $R_2$ is hydrogen, $R_1$ and $R_2$ are each hydrogen, or together $R_1$ and $R_2$ are =O; $R_3$ is hydrogen and $R_4$ is hydroxyl, $R_3$ is hydroxyl and $R_4$ is hydrogen, $R_3$ and $R_4$ are each hydrogen, or together $R_3$ and $R_4$ are =O; $R_5$ is hydrogen or hydroxyl; and $R_6$ is hydrogen or halogen.

17 Claims, No Drawings

4,5-SECOANDROSTANES

SUMMARY OF THE INVENTION

Compounds having the formula

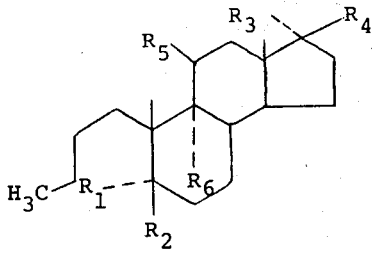

have useful anti-inflammatory activity. In formula I, and throughout the specification, the symbols are as defined below:

$R_1$ is hydrogen and $R_2$ is hydroxyl, $R_1$ is hydroxyl and $R_2$ is hydrogen, $R_1$ and $R_2$ are each hydrogen, or together $R_1$ and $R_2$ are =O;

$R_3$ is hydrogen and $R_4$ is hydroxyl, $R_3$ is hydroxyl, $R_4$ is hydrogen, $R_3$ and $R_4$ are each hydrogen, or together $R_3$ and $R_4$ are =O;

$R_5$ is hydrogen or hydroxyl; and $R_6$ is hydrogen or halogen (the preferred halogen bein fluorine).

DETAILED DESCRIPTION OF THE INVENTION

The novel 4,5-secoandrostanes of formula I are physiologically active substances possessing useful anti-inflammatory activity, as demonstrated by the carrageenin- induced edema assay, adn can be used in various mammalian species such as domestic animals, e.g., dogs and cats. They can be used to decrease joint swelling, tenderness, pain, and stiffness in conditions such as rheumatoid arthritis. It is a particularly beneficial property of these 4,5-secoandrostanes that they exhibit their anti-inflammatory activity without exhibiting the endocrine profile of their steroid precursors.

A 4,5-secoandrostane of formula I can be compounded according to accepted pharmaceutical practice, in oral dosage forms such as tablets, capsules, elixirs or powders for administration in a dosage range of from about 100mg/70kg/day to 2g/70kg/day, preferably from about 100mg/70kg/day to 1g/70kg/day, in single or multiple doses.

The compounds of this invention are prepared from 4-androsten-3-ones having the formula

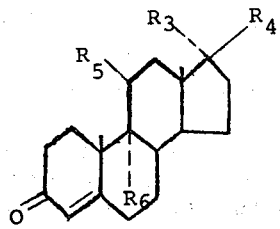

The 4-androsten-3-ones of formula II are known; see for example Feiser et al., Steroids, Reinhold Publishing Corp. (1959); Fried, United States patent no. 3,072,684; Alvarez, Steroids, 2:393 (1963); and Fetizon, Bull, Soc. Chim. France 1966 (3), 850.

Reaction of a 4-androsten-3-one of formula II with hydrogen peroxide in the presence of alkali; e.g., potassium hydorxide, sodium hydroxide, etc. yields a 4,5-epoxy steroid having the formula

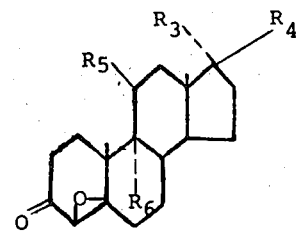

The reaction is run in a polar organic solvent, preferably a lower alkanol such as methanol. When $R_6$ is hydrogen, the reaction will preferably be run at a reduced temperaure for about 2 hours to 1 day, preferably from about 2 hours to 8 hours. When $R_6$ is a halogen, the reaction will preferably be run at room temperature for from about 3 to 7 days.

Reaction of 4,5-epoxy steroid of formula III with p-toluenesulfonylhydrazide yields a 4,5-seco-3-androstyn-5-one having the formula

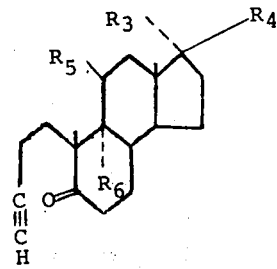

The reaction is run in an organic solvent or a mixture of organic solvents such as acetic acid or halogenated hydrocarbons. Reaction conditions are not critical and the reaction can conveniently be run at room temperature. The 4,5-seco-3-androstyn-5-ones of formula IV can be reduced to the corresponding 4,5-seco-5-androstanone by reaction with gaseous hydrogen in the presence of a catalyst such as palladium or platinum oxide.

The 4,5-seco-5-androstanones have the formula

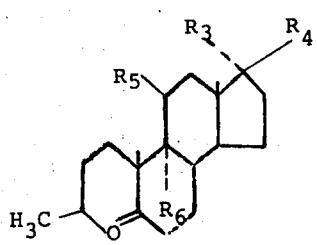

The compounds of formula V can be reduced to the corresponding 5-hydroxy compounds by reaction with sodium borohydride. The reaction can be run in a lower alkanol such as methanol. If, however, the compound of formula V contains an oxo group in the 17-position, this will also be reduced to a hydroxyl group.

Those compounds of formula I having a 5-hydroxy group and a 17-oxo group can be prepared from the corresponding 17-hydroxy compound of formula V. The conversion can be effected as follows: protect the 17-hydroxy group (e.g., by acylation), convert the 5-oxo group to a 5-hydroxy group (e.g., by reduction with sodium borohydride as described above), protect the 5-hydroxy group with a protecting group different than the one used to protect the 17-hydroxy group, remove the protecting group at the 17-position, convert the 17-hydroxy group to an oxo group (e.g., by reaction with chromium troxide in an organic solvent in the presence of an organic base such as pyridine), and remove the protecting group at the 5-position.

Those compounds of formula I that are unsubstituted in the 5- and 17-positions, or unsubstituted in the 5-position having a hydroxy group in the 17-position, can be prepared from the corresponding 5-oxo compound of formula V by reaction with a mixture of a hydrazine and ethylene glycol in the presence of alkali (e.g., potassium hydroxide). The reaction is preferably run under reflux conditions.

Those compounds of formula I that are unsubstituted in the 5-position havving a 17-oxo group can be prepared by oxidizing the corresponding 17-hydroxy compound as described above.

Those compounds of formula I wherein at least one of $R_1$, $R_2$, $R_3$ and $R_4$ is other than hydrogen are preferred.

The following examples are specific embodiments of this invention.

EXAMPLE 1

17$\beta$-Hydroxy-4,5-seco-5-androstanone

A. 4$\beta$,5-Epoxy-17$\beta$-hydroxy-3-androstanone

A solution of 33g of testosterone in 1500ml of methanol is prepared and cooled in an ice bath to 3°C. Over an hour period, 191ml of 4N sodium hydroxide and 143ml of 30% hydrogen peroxide are added simultaneously. The mixture is stirred at 3° C for an additional 3 hours after which thin layer chromatography shows that the testosterone has been completely consumed. The mixture is poured into 20 gallons of ice water contain 3 pounds of salt and the title epoxide crysallizes. The crystalline material is filtered with suction and the residue is washed with water on the filter and dried to yield 10.5g of the title compound.

B. 17$\beta$-Hydroxy-4,5-seco-3-androstyn-5-one

4$\beta$,5-Epoxy-17$\beta$-hydroxy-3-androstanone (10.5g) is dissolved in 375ml of methylene chloride-acetic acid (1:1) and the solution is chilled to 0°C. A solution of 6.42g of p-toluenesulfonylhydrazide in 375ml of methylene chloride-acetic acid (1:1) is added dropwise over a 1-hour period. The mixture is stirred at room temperature for about 16 hours and poured into water. The organic layer is separated, washed with water and sodium bicarbonate and then dried over sodium sulfate. Evaporation of the solvents yields a material which is purified on a 300ml silica gel column using methylene chloride-pentane (1:1) as the eluent. The title compound (8.5g) is isolated as a viscous oil.

C. 17$\beta$-(Acetyloxy)-4,5-seco-3-androstyn-5-one

17$\beta$-Hydroxy-4,5-seco-3-androstyn-5-one (8.5g) is combined with 10 ml of acetic anhydride in 50ml of pyridine and the mixture heated at reflux for 1 hour. It is then poured into water and stirred for 2 hours. The mixture is extracted with three 100ml portions of methylene chloride, washed with water, dried over sodium sulfate and evaporated to yield a crystalline material. Purification on a 200ml silica gel column using hexane-benzene as the eluent and recrystallization from aqueous methanol yields 6.7g of the title compound, melting point 90°–92° C.

D. 17$\beta$-Hydroxy-4,5-seco-5-androstanone

17$\beta$-(Acetyloxy)-4,5-seco-3-androstyn-5-one (6.7g) is dissolved in 300ml of ethyl acetate, mixed with 300mg of 10% palladium on charcoal and treated with gaseous hydrogen at atmospheric pressure. After 90 minutes, the reaction mixture has consumed 930ml of hydrogen and the reaction is complete. The mixture is filtered and the solvent removed under a vacuum yielding a viscous oil. The oil is dissolved in 200ml of methanol, treated with 20ml of saturated potassium carbonate solution and stirred at room temperature overnight. The solvent is removed under vacuum and the residue is partitioned between water and methylene chloride. The organic layer is dried over sodium sulfate and concentrated to yield a crystalline product. This purified on a 300ml silica gel column using methylene chloride-pentane (1:1) as the eluent. Recrystallization of the material isolated from aqueous methanol yields 4.2g of the title compound, melting point 106°–108° C.

EXAMPLE 2

4,5-Secoandrostane-5,17-dione

Chromium trioxide (4.06g) and 6.64ml of anhydrous pyridine are added to 200ml of anhydrous dichloromethane and the solution is stirred at room temperature for 15 minutes the solution is stirred at room temperature for fifteen minutes in a nitrogen atmosphere. A solution of 17 $\beta$-hydroxy-4,5-seco-5-androstanone (2g, prepared as described in Example 1) in 50ml of anhydrous dichloromethane is added to the solution along with 10g of dry Celite, and the mixture is stirred for 15 minutes. The mixture is filtered and the Celite cake is washed with dichloromethane. The filtrate is then washed with 5% sodium hydroxide, 5of hydrochloric acid, 5% sodium bicarbonate and water. The dichloromethane solution is dried over anhydrous sodium sulfate and concentrated in vacuo. The resultant oil is distilled in vacuo to yield 1.9g. of the title compound, boiling point 160° C at 0.001mm. of Hg.

EXAMPLE 3

9-Fluoro-11$\beta$-hydroxy-4,5-seco-5,17-androstanedione

A.

4$\beta$,5-Epoxy-9-fluoro-11$\beta$-hydroxyandrostane-3,17-dione

A solution of 10g of 9-fluoro-11$\beta$-hydroxyandrost-4-ene-3,17-dione in 1.5 liter of methanol is stirred at room temperature with 30ml of 30% hydrogen peroxide and 20ml of 4N sodium hydroxide solution. The resulting solution is diluted with 4 liters of water and extracted with dichloromethane. The dichloromethane solution is washed with 5% hydrochloric acid, 5% sodium bicarbonate solution, water, dried, and evaporated in vacuo to give 9.1g of crude product. This material is dissolved in dichloromethane and chromatographed on a 100g-silica gel column. Elution with the same solvent gives 3.39g of the title compound and some impure material which is rechromatographed to give a further 1.71g of the title compound.

B.
9-Fluoro-11β-hydroxy-4,5-secoandrost-3-yne-5,17-dione

A solution of 5.1g of 4β,4-epoxy-9-fluoro-11β-hydroxyandrostane-3,17-dione in 300ml of 1:1 dichloromethaneacetic acid is cooled to 0°C and a solution of 2.8g of p-toluenesulfonylhydrazine in 300ml of the same solvent is added. After stirring overnight at room temperature, the solution is diluted with 1 liter of water and the dichloromethane layer is separated. The aqueous phase is extracted with dichloromethane and the combined solutions are washed with water, 5% sodium bicarbonate solution, and dried. Solvent removal in vacuo gives 5.75g of material which is chromatographed on a 60g-silica gel column. Elution with dichloromethane gives 3.09g of the title compound.

C.
9-Fluoro-11β-hydroxy-4,5-seco-5,17-androstanedione

A solution of 3.0g of 9-fluoro-11β-hydroxy-4,5-secoandrost-3-yne-5,17-dione in 250ml of ethyl acetate is stirred in an atmosphere of hydrogen with 300mg of 5% Pd/C. After 135 minutes hydrogen uptake (520ml) ceases and the catalyst is filtered. The filtrate is evaporated in vacuo and the residue is dissolved in dichloromethane and filtered through silica gel. Elution with dichloromethane and recyrstalliztion gives 2.52g. of the title compound, melting point 172–174°C.

EXAMPLE 4

4,5-Secoandrostane-5β,17β-diol and
4,5-Secoandrostane-5α, -17β-diol

A mixture of 17β-hydroxy-4,5-seco-5-androstanone (2.92g, prepared as described in Example 1), 380mg of sodium borohydride, and 50ml of methanol is prepared and stirred for 1 hour at room temperature. An additional 100mg of sodium borohydride is added and stirring is continued for an additional 30 minutes. Sodium borohydride (100mg) is again added to the reaction mixture and stirring is continued for an additional 30 minutes. The mixture is concentrated in vacuo and the residue is diluted with water. The product is extracted with dichloromethane which on concentration yields a mixture of 5α and 5β alcohols. The two alcohols are separated by column chromatography on silica gel with dichloromethane as the eluent, yielding 1.7g of 4,5-secoandrostane-5β,17β-diol, melting point 126°–129° C and 580mg of 4,5-secoandrostane-5α,17β-diol, melting point 109°–111° C.

EXAMPLE 5

17β-Hydroxy-4,5-secoandrostane

A mixture of 8.0g of 17β-hydroxy-4,5-seco-5-androstanone (prepared as decribed in Example 1), 16ml of 100% hydrazine hydrate and 48ml of ethylene glycol is prepared and heated at reflux for one hour. Potassium hydroxide is added and the temperature is raised to 210° C by allowing water to boil off. Refluxing is continued for 8 hours. The mixture is poured into water and the product is extracted with methylene chloride yielding 8.0g of crude product which is purified on 500ml of silica gel using methylene chloride as the eluent. The product is collected and concentrated to yield 6.0g of the title compound which is further purified by sublimation at 85° C. The product has a melting point of 92°–93° C.

EXAMPLE 6

4,5-Seco-17-androstanone

A mixture of 9.3g of chromium trioxide, 15ml of pyridine and 380ml of anhydrous methylene chloride is allowed to stir at room temperature for 15 minutes. A solution of 17β-hydroxy-4,5-secoandrostane (4.3g, prepared as described in Example 5) in 20ml of methylene chloride and 18g of dry Celite are added to the mixture. The resulting mixture is stirred for 15 minutes and filtered with suction. The residue is washed on the filter with methylene chloride and the filtrate is washed successively with two 100ml portions of 5% sodium hydroxide, two 100ml portions of water, two 100ml portions of 5% hydrochloric acid an an additional two 100ml portions of water. The purified filtrate is dried over sodium sulfate and concentrated to yield 4.5g of crude product. A 1.5g portion of the crude product is distilled, yielding 1.4g of the title compound, boiling point 130-135°C at 0.001mm. of Hg.

EXAMPLE 7

4,5-Secoandrostane

A mixture of 4,5-seco-17-androstanone (2.7g, prepared as described in Example 6), 5.4ml of 100% hydrazine hydrate and 18ml of ethylene glycol is heated at reflux for 6 hours. Potassium hydroxide (2.7g) is added and water is allowed to escape until the pot temperature reaches 210°C. Heating under reflux conditions is continued for an additional 6 hours at which time the reaction mixture is poured into water. The aqueous mixture is extracted with methylene chloride and the extract is dried over sodium sulfate and concentrated. This is purified on 50ml of silica gel using hexane as the eluent. The resultant oil is distilled in vacuo to yield 600mg of the title compound, boiling point 110°–120° C at 0.01mm of Hg.

EXAMPLE 8

4,5-Seco-5-androstanone

A. 4β,5-Epoxy-3-androstanone

4-Androstene-3-one (4.3g) is dissolved in 300ml of methanol and cooled to 3° C in an ice-water bath. To the cooled mixture is added 20ml of 30% hydrogen peroxide and 26ml of 4N sodium hydroxide solution simultaneously from 2 dropping funnels. The addition is carried out in a nitrogen atmosphere with stirring. The mixture is allowed to warm to room temperature and stirring is continued for an additional hour. The mixture is diluted with 4 liters of water and extracted with methylene chloride. The organic layer is dried over sodium sulfate and concentrated to yield 3.0g of the title compound.

B. 4,5-Seco-3-androstyn-5-one

4β,5-Epoxy-3-androstanone is dissolved in 100ml of acetic acid-methylene chloride (50:50) and cooled to 3° C in an ice-water bath. A solution of 2.8g of p-toluenesulfonyl hydrazide in 100ml of the same solvent is added dropwise under a nitrogen blanket with stirring. The mixture is maintained at room temperature for one hour and then poured into water and extracted with methylene chloride. The methylene chloride extract is washed with 5% sodium hydroxide solution and dried over sodium sulfate. Concentration yields 3.0g of a mixture of the title compound and the corresponding hydrazone. The hydrazone is converted to the ketone by refluxing overnight in acetone. Purification of the material on silica gel using methylene chloride-hexane (40:60) yields 1.3g of the title compound.

C. 4,5-Seco-5-androstanone 4,5-Seco-3-androstyn-5-one (1.3g) is hydrogenated over 200mg of 10% palladium on charcoal in 50ml of ethyl acetate. After 40 minutes 180ml of hydrogen has been absorbed and the mixture is filtered to remove the catalyst and concentrated in vacuo. The material is distilled in vacuo to yield 1.2g of material. Examination of the material shows that hydrogenation is not complete and the material is again hydrogenated and distilled to yield 1.0g of the title compound, boiling point 115°–120° C at 0.001mm of Hg.

EXAMPLE 9

5α-Hydroxy-4,5-secoandrostane

A solution of 1.8g of 4,5-seco-5-androstanone (prepared as described in Example 8) in 50ml of methanol is cooled to 15° C and 500mg of sodium borohydride is added. The mixture is stirred at room temperature for 30 minutes followed by the addition of an additional 500mg of sodium borohydride and additional stirring for 30 minutes. The mixture is then poured into water and extracted with methylene chloride. When concentrated, the methylene chloride extracts yield a solid product which is a mixture of two compounds. The two compounds are separated by column chromatography on 500ml of silica gel using methylene chloride-pentane (50:50) as the eluent. The title compound (900mg) is collected and has a melting point of 113°–115° C.

EXAMPLE 10

5α-Hydroxy-4,5-seco-17-androstanone

A. 17α-(Acetyloxy)-4,5-seco-5-androstanone

A solution of 17β-hydroxy-4,5-seco-5-androstanone (prepared as described in Example 1) in pyridine and acetic anhydride is reacted at room temperature for 4 hours and the solvent evaporated in vacuo to yield the title compound.

B. 17β-(Acetyloxy)-5β-hydroxy-4,5-secoandrostane

17β-(Acetyloxy)-4,5-seco-5-androstanone is dissolved in methanol and treated at 0° C with sodium borohydride. The resulting mixture is stirred, poured into water and the product separated and isolated by filtration. The title compound is separated by column chromatography.

C. 17β-(Acetyloxy)-5β-hydroxy-4,5-secoandrostane, tetrahydropyranyl ether

17β-(Acetyloxy)-5β-hydroxy-4,5-secoandrostane is combined with p-toluenesulfonic acid and dihydropyran in anhydrous benzene. The mixture is heated at reflux for 24 hours, poured into sodium bicarbonate solution and the product extracted with methylene chloride.

D.

5α,17β-Dihydroxy-4,5-secoandrostane-5-tetrahydropyranyl ether

17β-(Acetyloxy)-5α-hydroxy-4,5-secoandrostane, tetrahydropyranyl ether is combined with saturated potassium carbonate in methanol-dioxane (50:50) and stirred for ,516 hours. The reaction mixture is poured into water and the product is extracted with methylene chloride.

E.

5α-Hydroxy-4,5-seco-17-androstanone-5-tetrahydropyranyl ether

A mixture of chromium trioxide and pyridine is prepared in anhydrous methylene chloride. After 15 minutes at room temperature, dry Celite is added followed by 5α,17β-dihydroxy-4,5-secoandrostane-5-tetrahydropyranyl ether. The resulting mixture is stirred at room temperature for an additional 15 minutes and filtered to yield the title compound.

F. 5α-Hydroxy-4,5-seco-17-androstanone

5α-Hydroxy-4,5-seco-17-androstanone-5-tetrahydropyranyl ether is dissolved in methanol and treated with concentrated hydrochloric acid at room temperature. After one hour, the mixture is poured into water and the title compound is extracted with methylene chloride.

What is claimed is:

1. A compound having the formula

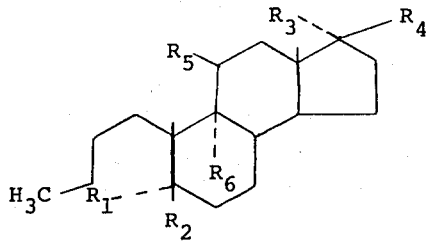

wherein $R_1$ is hydrogen and $R_2$ is hydroxyl, $R_1$ is hydroxyl and $R_2$ is hydrogen, $R_1$ and $R_2$ are each hydrogen, or together $R_1$ and $R_2$ are $=O$; $R_3$ is hydrogen and $R_4$ is hydroxyl, $R_3$ is hydroxyl and $R_4$ is hydrogen, $R_3$ and $R_4$ are each hydrogen, or together $R_3$ and $R_4$ are $=O$; $R_5$ is hydrogen or hydroxyl; and $R_6$ is hydrogen or halogen.

2. A compound in accordance with claim 1 wherein at least one of $R_1$, $R_2$, $R_3$ and $R_4$ is other than hydrogen.

3. A compound in accordance with claim 1 wherein $R_5$ is hydrogen.

4. A compound in accordance with claim 1 wherein $R_5$ is hydroxyl.

5. A compound in accordance with claim 1 wherein $R_6$ is hydrogen.

6. A compound in accordance with claim 1 wherein $R_6$ is fluorine.

7. A compound in accordance with claim 1 having the formula

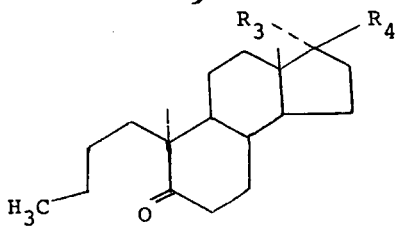

8. The compound in accordance with claim 1 having the name 17β-hydroxy-4,5-seco-5-androstanone.

9. The compound in accordance with claim 1 having the name 4,5-secoandrostane-5,17-dione.

10. The compound in accordance with claim 1 having the name 9-fluoro-11β-hydroxy-4,5-seco-5,17-androstanedione.

11. The compound in accordance with claim 1 having the name 4,5-secoandrostane-5β,17β-diol.

12. The compound in accordance with claim 1 having the name 4,5-secoandrostane-5α,17β-diol.

13. The compound in accordance with claim 1 having the name 17β-hydroxy-4,5-secoandrostane.

14. The compound in accordance with claim 1 having the name 4,5-seco-17-androstanone.

15. The compound in accordance with claim 1 having the name 4,5-secoandrostane.

16. The compound in accordance with claim 1 having the name 4,5-seco-5-androstanone.

17. The compound in accordance with claim 1 having the name 5α-hydroxy-4,5-secoandrostane.

* * * * *

UNITED STATES PATENT AND TRADEMARK OFFICE
CERTIFICATE OF CORRECTION

PATENT NO. : 3,984,474
DATED : October 5, 1976
INVENTOR(S) : Peter W. Sprague et al.

It is certified that error appears in the above-identified patent and that said Letters Patent are hereby corrected as shown below:

Column 1, line 26, should read:
-- $R_3$ is hydrogen and $R_4$ is hydroxyl, $R_3$ is hydroxyl and $R_4$ --

Column 1, line 37, "adn" should read -- and --.

Column 3, line 3, "formrula" should read -- formula --.

Column 3, line 49, "contain" should read -- containing --.

Column 4, line 1, the title of C. should read:

C. 17β-(Acetyloxy)-4,5-seco-3-androstyn-5-one

Column 8, line 8, ",516 hours" should read -- 16 hours --.

Signed and Sealed this

Twenty-second Day of March 1977

[SEAL]

Attest:

RUTH C. MASON
*Attesting Officer*

C. MARSHALL DANN
*Commissioner of Patents and Trademarks*